United States Patent
Eck et al.

(10) Patent No.: US 6,414,190 B1
(45) Date of Patent: Jul. 2, 2002

(54) PURIFICATION OF ACRYLIC ACID BY CRYSTALLIZATION BY MEANS OF VACUUM EVAPORATION

(75) Inventors: Bernd Eck, Viernheim; Jörg Heilek, Bammental; Volker Schliephake, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/357,955

(22) Filed: Jul. 21, 1999

(30) Foreign Application Priority Data

Jul. 22, 1998 (DE) .......................... 198 32 962

(51) Int. Cl.$^7$ .............................. C70C 51/42
(52) U.S. Cl. ...................................... 562/600
(58) Field of Search ........................ 562/600

(56) References Cited

FOREIGN PATENT DOCUMENTS

GB          1 293 848    * 10/1972
JP          7-82210      3/1995

* cited by examiner

Primary Examiner—Gary Geist
Assistant Examiner—Farhad Forohar
(74) Attorney, Agent, or Firm—Oblon, Spivak, McClelland, Maier & Neustadt, P.C.

(57) ABSTRACT

In a process for purifying acrylic acid by crystallization by means of vacuum evaporation, a solution which contains acrylic acid and water and may contain further components is crystallized by means of vacuum evaporation with formation of a liquid phase, consisting of a mother liquor containing more than 10% by weight of water and of the crystals, and a vapor phase, the vapor phase is introduced into a liquid material in a condensation zone with formation of a liquid condensation mixture, and the liquid condensation mixture is recycled at least partly to the condensation zone, the operating conditions in the condensation zone being established so that no solid is precipitated.

18 Claims, 2 Drawing Sheets

PURIFICATION OF ACRYLIC ACID BY CRYSTALLIZATION BY MEANS OF VACUUM EVAPORATION

Figure 1:
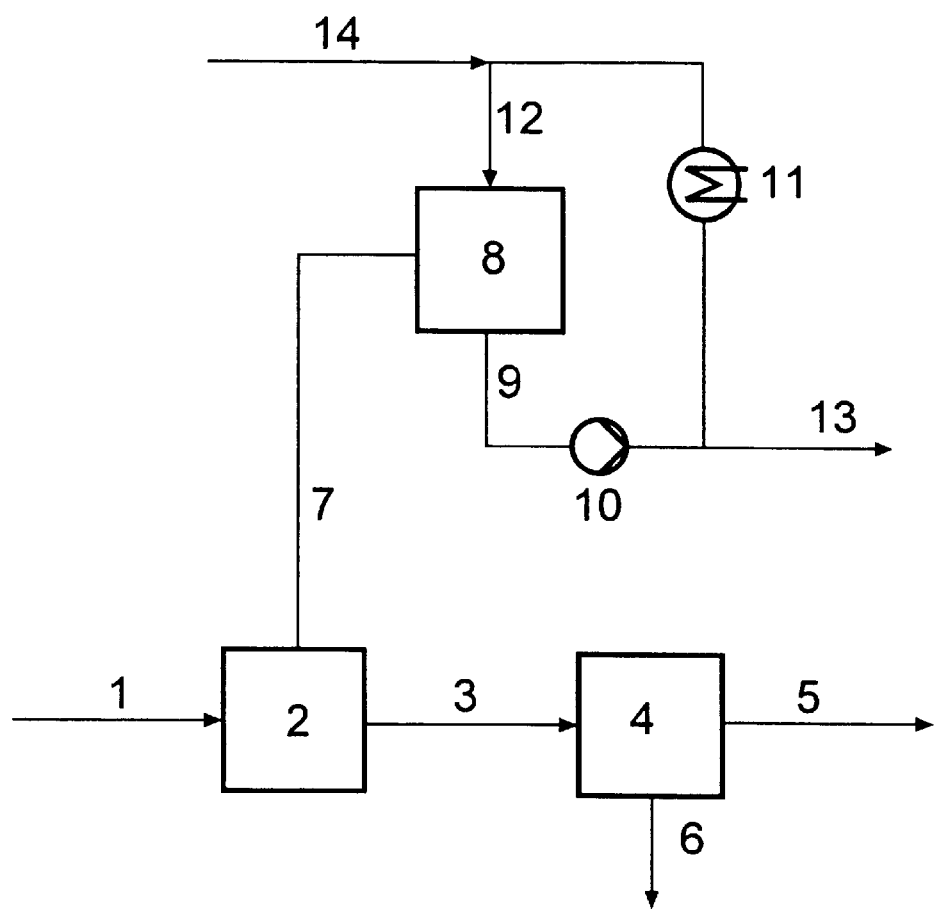

The present invention relates to a process for purifying acrylic acid by crystallization by means of vacuum evaporation.

Crystallization processes for purifying acrylic acid are known. In crystallization processes based on the generation of supersaturation required for solids formation, a distinction is generally made between cooling crystallization processes and evaporative crystallization processes. Whereas, in cooling crystallization, solids formation is effected by cooling the solution to be crystallized, in evaporative crystallization the solubility limit of the solid to be crystallized in the solution is exceeded by evaporating one or more components of the solution (solvent withdrawal). If the evaporation is carried out under reduced pressure (vacuum evaporation), the crystallizing solution can be additionally cooled by the reduced pressure applied. Crystallization by means of evaporative cooling, in which no heat is supplied and the crystallization is thus carried out as an adiabatic vacuum evaporative crystallization, is to be regarded as a special case of crystallization by means of vacuum evaporation. The vapor leaving the crystallization apparatus in the vacuum evaporative crystallization is usually condensed in a condensation stage. In an evaporative cooling crystallization, some or all of the condensed vapor is usually recycled to the crystallization apparatus (reflux of the condensate into the crystallization). Evaporative cooling as a vacuum evaporation process is therefore situated between the pure cooling process and the pure evaporation process (without reflux of the condensed vapor).

Compared with a cooling crystallization process operating with indirect cooling by means of heat exchangers, the evaporative cooling process has a major advantage of direct cooling of the solution to be crystallized (direct withdrawal of the heat of vaporization from the solution to be crystallized). Operating problems due to incrustations, as may occur in the heat exchangers in indirect cooling, are thus avoided.

The Laid-Open Japanese Patent Application JP 07 082 210-A discloses a process for purifying acrylic acid by crystallization by means of evaporative cooling. In this process, the starting material used is a crude acid which contains little or no water, and water is added to it in order to bring the water content of the mother liquor present during the crystallization to a range of from 2 to 10% by weight. Parts of the acrylic acid/water mixture are evaporated in order to induce adiabatic cooling under reduced pressure, with the result that acrylic acid crystals are precipitated, which are then isolated. The vapor formed during evaporation is passed into a condenser, acrylic acid flowing over the surface of the condenser in order to prevent ice formation, or water flowing over the surface of the condenser in order to prevent precipitation of acrylic acid crystals. The condensate is recycled to the crystallization.

In the light of this prior art, it is an object of the present invention to provide a process which permits the purification of acrylic acid from a crude acid having a relatively high water content, solids formation in the condenser being avoided.

We have found that this object is achieved by crystallizing the acrylic acid from a water-containing solution by means of vacuum evaporation with formation of a liquid phase, consisting of an acrylic acid-containing solution containing more than 10% by weight of water (mother liquor) and the crystals, and a vapor phase, introducing the vapor phase into a liquid material in a condensation zone with the formation of a liquid condensation mixture and recycling the condensation mixture at least partly to the condensation zone.

The present invention therefore relates to a process for purifying acrylic acid by crystallization by means of vacuum evaporation, wherein a solution which contains acrylic acid and water and may contain further components is crystallized by means of vacuum evaporation with formation of a liquid phase, consisting of a mother liquor containing more than 10% by weight of water and of the crystals, and a vapor phase, the vapor phase is introduced into a liquid material in a condensation zone with formation of a liquid condensation mixture or condenser mixture, and the liquid condensation mixture is recycled at least partly to the condensation zone, the operating conditions in the condensation zone being established so that no solid is precipitated therein.

Preferred embodiments of the invention are described in the subclaims, in the following description of the Figures and in the Example. Here, the terms "condenser mixture" and "condensation mixture" have the same meaning. The terms "low-boiling components" and "medium-boiling components" relate to components which have, respectively, a lower boiling point than acrylic acid and about the same boiling point as acrylic acid.

Figure 2:
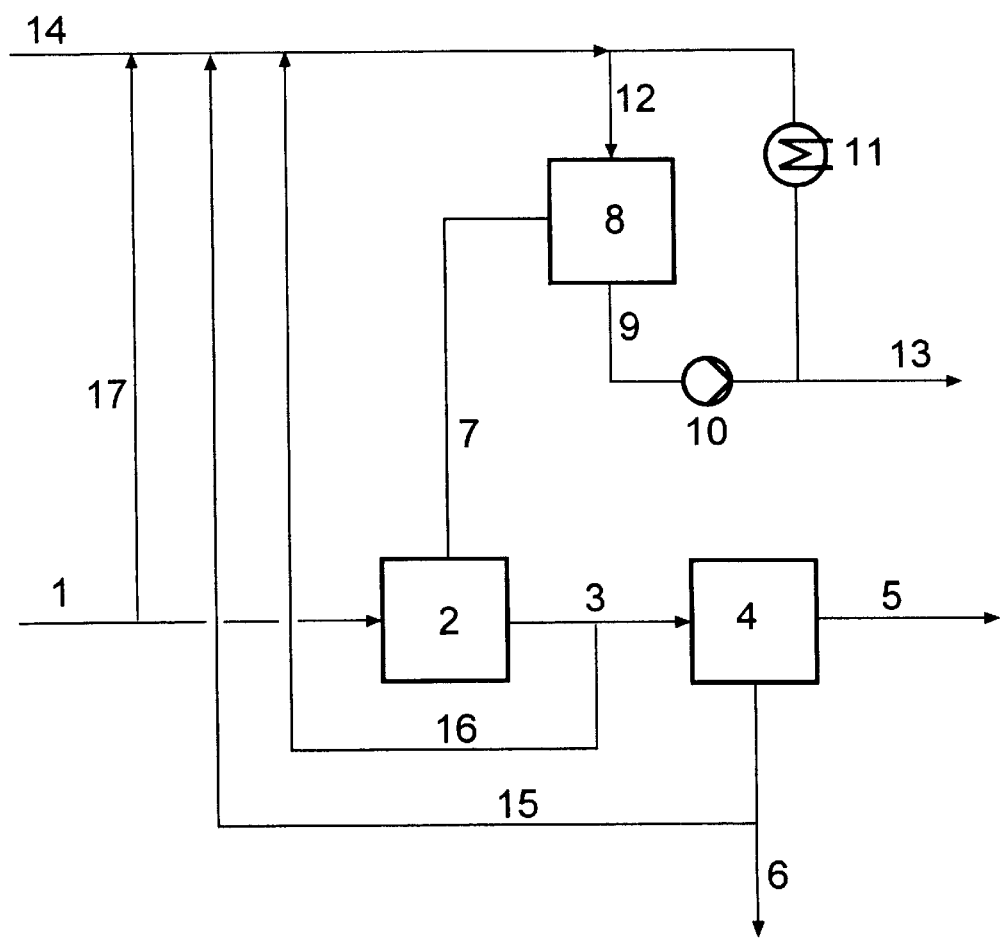

In the Figures:

FIG. 1 shows a scheme for carrying out a preferred process according to the invention, external auxiliary liquids being added to recycled condensation mixture; and FIG. 2 shows a scheme for carrying out a preferred process according to the invention, external and/or internal auxiliary liquids being added to recycled condensation mixture.

Suitable solutions from which the acrylic acid can be obtained according to the invention contain preferably from 50 to 97, in particular from 65 to 95, most preferably from 70 to 90, % by weight of acrylic acid and from 3 to 50, in particular from 5 to 35, most preferably from 10 to 30, % by weight of water, based in each case on 100% by weight of acrylic acid and water. In addition to the acrylic acid and the water, the solution to be crystallized may contain further components, impurities or secondary components in an amount of from 0 to 15, in particular from 0.3 to 10, most preferably from 0.5 to 5, parts by weight, based in each case on 100 parts by weight of acrylic acid and water. The further components/secondary components are in particular secondary components, such as acetic acid, propionic acid, formaldehyde, further aldehydes, maleic anhydride, low-boiling and medium-boiling components and unconverted propene or acrolein, which result during the preparation of acrylic acid by catalytic gas-phase oxidation of propene/acrolein.

The crystallization methods and apparatuses used are in principle not subject to any restriction. All crystallization methods in which the crystallizing solution is thoroughly mixed by stirring or circulation are suitable, both continuous and batchwise procedures. Preferably used apparatuses are stirred kettle crystallizers and forced circulation crystallizers, but draught-tube crystallizers and fluidized-bed crystallizers may also be used. The crystallization is carried out by means of adiabatic or nonadiabatic vacuum evaporation, i.e. the evaporation is effected under reduced pressure either with heat supply (nonadiabatic) or without heat supply (adiabatic; evaporative cooling). In the case of nonadiabatic vacuum evaporation, the heat is supplied via conventional heat exchangers, which are not subject to any restriction. Expediently, crystallizers having external heat exchangers or having wall heating are used. The crystallization is preferably carried out under reduced pressure of from 1 to 8, in particular from 2 to 5, mbar (absolute) and at from −12 to +5° C., in particular from −5 to +5° C.

The vapor phase forming during the crystallization consists for the most part of water and acrylic acid but may also contain amounts of the further components/secondary components, in particular acetic acid, propionic acid, aldehydes and low-boiling and medium-boiling components. The liquid phase furthermore forming during the crystallization contains the acrylic acid crystals, which can be isolated from the mother liquor by any known solid-liquid separation method. Advantageously, the crystals are isolated by filtration, sedimentation and/or centrifuging of the mother liquor, and the crystals can additionally be washed with suitable wash liquids.

The water content of the mother liquor is brought to more than 10% by weight of water, based on 100% by weight of mother liquor. The water content to be established for the mother liquor is preferably from 10 to 34, more preferably from 10 to 25, most preferably from 10 to 20, % by weight, based in each case on 100% by weight of mother liquor, of water. In addition to the water, the mother liquor furthermore contains acrylic acid and may contain further components/secondary components. The water content of the mother liquor can be readily established by a person skilled in the art by means of the pressure present in the crystallization and/or by means of the amount of water fed into the crystallization.

The liquid material into which the vapor phase is introduced or condensed or absorbed is not subject to any particular restriction per se. Suitable liquid materials are all those which, during/after introduction of the vapor phase, lead to a liquid condensation mixture above which the components of the vapor which are to be condensed or absorbed have partial pressures which are lower than the partial pressures of these components above the crystallizing solution and whose freezing point is lower than the condensation or absorption temperature. Here, the stream which is introduced into the condensation zone in addition to the vapor is referred to as liquid material, while the stream which leaves the condensation is referred to as condensation mixture.

In a preferred embodiment, the liquid material is a one-phase liquid mixture which contains from 40 to 75, in particular from 50 to 70, preferably from 62 to 67, most preferably from 65 to 66, % by weight of acrylic acid and from 25 to 60, in particular from 30 to 50, preferably from 33 to 38, most preferably from 34 to 35, % by weight of water, based in each case on 100% by weight of acrylic acid and water. Expediently, the liquid material is prepared using the solution to be crystallized, mother liquor arriving from the crystallization, liquid phase which contains crystals, or a mixture thereof.

In continuous operation, it is possible to add to recycled condensation mixture an auxiliary liquid by means of which the acrylic acid content of the liquid material thus produced is brought to a range of preferably from 50 to 70, in particular from 65 to 66, % by weight, based in each case on 100% by weight of acrylic acid and water, of acrylic acid, depending on the vapor composition and amount of vapor. This auxiliary liquid is preferably an internal auxiliary liquid, i.e. a liquid which originates from the system and in which no assistants foreign to the system are used, and whose acrylic acid content is at least 65, in particular from 65 to 95, most preferably from 70 to 90, % by weight, based in each case on 100% by weight of acrylic acid and water. Particularly suitable internal auxiliary liquids are solution to be crystallized, mother liquor arriving from the crystallization, liquid phase which contains crystals, or a mixture thereof. An external auxiliary liquid may also be used. In a preferred embodiment of the process, the external auxiliary liquid is chosen so that, as a result of its introduction in an amount of at least 5, in particular from 5 to 70, most preferably from 5 to 30, % by weight, based in each case on the condenser mixture, the freezing point of the condenser mixture is reduced below the freezing point of the eutectic acrylic acid/water mixture(−12° C.). Preferred examples of external auxiliary liquids are acetic acid and mixtures of acrylic acid and water which have a high content of acetic acid. The use of an external auxiliary liquid leads to even greater temperature differences in the heat transfer in the condensation and thus permits the use of more compact and more economical apparatuses. However, it may necessitate the separate working-up or disposal of the condenser mixture.

The operating conditions in the condensation zone for preventing precipitation of solid therein are determined by the choice of the liquid material and by the freezing point of the condensation mixture. Within these parameters and on the basis of the present description, a person skilled in the art can easily find suitable values by customary experiments.

In a preferred embodiment of the invention, the temperature of the liquid condenser mixture is lower than the saturation vapor temperature of the vapor phase.

The condensation methods and apparatuses and the production of the mass-transfer and heat-exchange surfaces required for the condensation are not subject to any restrictions at all. The transfer surface required for heat removal can be introduced as surface condenser into the condensation stage itself or may be present in the circulation outside the condensation apparatus, which is then in the form of a mixing condenser with or without baffles or may be a combination of the two variants. An external, simple and economical heat exchanger, for example a plate-type heat exchanger, is preferred. The mixing of vapor and liquid material is preferably effected by spraying the liquid material and/or by trickling the liquid material over apparatus surfaces, baffles and/or packings of the condenser.

According to the invention, the condenser mixture is at least partly recycled to the condensation zone. The recycle ratio is preferably from 10:1 to 150:1, in particular from 20:1 to 150:1, most preferably from 50:1 to 150:1, based in each case on kg/h (mass flow rate) of recycled condenser mixture to kg/h of nonrecycled condenser mixture. Nonrecycled condenser mixture is removed from the process or, especially if no components over and above the components in the solution to be crystallized are present, is recycled to the crystallization.

FIG. 1 shows a preferred embodiment of the novel process. A solution 1 which contains the acrylic acid to be purified or to be obtained is fed to the crystallization 2, in which the water content of the mother liquor is kept above 10% by weight. The crystal suspension formed is fed via line 3 to the solid-liquid separation 4. The acrylic acid crystals isolated are removed via line 5, while the remaining mother liquor is removed via line 6. The vapor formed in the crystallization by means of vacuum evaporation is fed via line 7 to the condensation zone 8 and is mixed there with liquid material from line 12. Via the circulation/recycle line 9, the circulation pump 10 and the heat exchanger (external) 11, recycled condenser mixture, together with external auxiliary liquid from line 14, is fed or recycled as liquid material via line 12 to the condensation zone 8. Nonrecycled condenser mixture is removed via line 13.

In FIG. 2, the same reference symbols denote the same thing as in FIG. 1. Compared with FIG. 1, FIG. 2 additionally has lines for feeding in auxiliary liquids. Mother liquor is fed via line 15, crystal suspension via line 16 and solution to be crystallized via line 17, in each case as auxiliary liquid to line 14, and via this to recycled condenser mixture.

In JP 07 082 210-A, acrylic acid is obtained from a crude acid with little or no water, the water content of the mother liquor present in the crystallization being brought to a range of from 2 to 10% by weight. At a higher water content in the mother liquor, formation of solid in the condenser would be expected in JP 07 082 210-A. In contrast, the novel process makes it possible to obtain acrylic acid from a crude acid having a higher water content without formation of solid occurring in the condenser. This is achieved by employing a water content of more than 10% by weight in the mother liquor and recycling at least a part of the condensation mixture.

The Example which follows and which is a preferred embodiment of the invention illustrates the invention.

EXAMPLE

An acrylic acid-containing solution of the composition stated in Table 1 was fed to a crystallization apparatus at a mass flow rate of 3340 g/h.

TABLE 1

| Component | Concentration in % by weight |
|---|---|
| Water | 12.8 |
| Acetic acid | 1.0 |
| Acrylic acid | 85.4 |
| Maleic acid | 0.3 |
| Acrolein | 0.008 |
| Propionic acid | 0.061 |
| Allyl acrylate | 0.2 |
| Furfural | 0.2 |
| Phenothiazine (PTZ) | 0.013 |

The crystallization apparatus used was a stirred container which had a suspension volume of 5 l and was equipped with a helical ribbon impeller. The heat evolved during the crystallization was removed by partial evaporation of the solution. The crystallization temperature was −1° C. and the pressure was 4.5 mbar absolute. The vapor generated at this pressure was condensed in a condenser in the form of a mixing condenser, with spraying of liquid material. For the preparation of the liquid material, initially an acrylic acid-containing solution which was identical in composition to the solution fed to the crystallization (composition according to Table 1) was used, by mixing 100 parts by weight of this solution with 30 parts by weight of water. The pressure in the condenser virtually corresponded to the pressure in the crystallization. The condenser mixture present in the condensation zone had a temperature of from −9 to −10° C. and the following composition according to Table 2.

TABLE 2

| Component | Concentration in % by weight |
|---|---|
| Water | 33.4 |
| Acetic acid | 0.04 |
| Acrylic acid | 64.8 |
| Maleic acid | 0.2 |

TABLE 2-continued

| Component | Concentration in % by weight |
|---|---|
| Acrolein | 0.067 |
| Propionic acid | 0.044 |
| Allyl acrylate | 0.2 |
| Furfural | 0.1 |
| PTZ | 0.008 |

A part-stream of 375 g/h of the condenser mixture leaving the condenser was removed. The other part-stream of about 26.5 kg/h was recycled to the condensation apparatus by mixing it with an acrylic acid-containing solution which was identical in composition to the solution fed to the crystallization (composition according to Table 1), as (internal) auxiliary liquid (cf. auxiliary liquid from line 14 in FIG. 1), with a mass flow rate of 220 g/h, and introducing this mixture as liquid material into the condensation zone and spraying it in the condenser. The suspension produced in the crystallization was separated into crystals and mother liquor on a 250 mm centrifuge at 1800 rpm and in a centrifuging time of 1 min. The mother liquor was obtained in an amount of 2070 g/h and had a composition according to the following Table 3.

TABLE 3

| Component | Concentration in % by weight |
|---|---|
| Water | 15.1 |
| Acetic acid | 1.4 |
| Acrylic acid | 82.3 |
| Maleic acid | 0.5 |
| Acrolein | 0.0015 |
| Propionic acid | 0.084 |
| Allyl acrylate | 0.21 |
| Furfural | 0.3 |
| PTZ | 0.02 |

After removal of the mother liquor in the centrifuge, the crystals were washed with molten crystals (300 g/h) at 1800 rpm for 1 min. 925 g/h of crystals were obtained. The molten crystals had the composition according to the following Table 4.

TABLE 4

| Component | Concentration in % by weight |
|---|---|
| Water | 0.46 |
| Acetic acid | 0.18 |
| Acrylic acid | 99.3 |
| Maleic acid | 0.019 |
| Acrolein | <0.001 |
| Propionic acid | 0.018 |
| Allyl acrylate | 0.01 |
| Furfural | 0.011 |
| PTZ | 0.0015 |

As is evident from the Example, the novel process permits the preparation of a purified acrylic acid from a crude acid containing almost 13% of water, a water content of 15.1% by weight being employed in the mother liquor in the crystallization and formation of solid in the condenser being avoided.

We claim:

1. A process for purifying acrylic acid by crystallization by means of vacuum evaporation, wherein a solution which contains acrylic acid and water and may contain further components is crystallized by means of vacuum evaporation with formation of a liquid phase, consisting of a mother liquor containing more than 10% by weight of water and of the crystals, and a vapor phase, the vapor phase is introduced into a liquid material in a condensation zone with formation of a liquid condensation mixture, and the liquid condensation mixture is recycled at least partly to the condensation zone, the operating conditions in the condensation zone being established so that no solid is precipitated therein.

2. A process as claimed in claim 1, wherein the solution contains from 50 to 97% by weight of acrylic acid and from 3 to 50% by weight of water, based in each case on 100% by weight of acrylic acid and water, and furthermore contains from 0 to 15 parts by weight, based on 100 parts by weight of acrylic acid and water, of further components.

3. A process as claimed in claim 1, wherein the crystallization is carried out at a pressure from 1 to 8 mbar (absolute).

4. A process as claimed in claim 1, wherein the water content of the mother liquor is brought to from 10 to 34% by weight.

5. A process as claimed in claim 1, wherein the liquid material used is a one-phase liquid mixture having an acrylic acid content of from 50 to 70% by weight, based on 100% by weight of acrylic acid and water.

6. A process as claimed in claim 1, wherein the liquid material is formed from recycled condensation mixture to which an internal auxiliary liquid having an acrylic acid content of at least 65% by weight, based on 100% by weight of acrylic acid and water, is added, this auxiliary liquid being selected from the group consisting of solution to be crystallized, mother liquor arriving from the crystallization, liquid phase which contains crystals, and a mixture thereof.

7. A process as claimed in claim 1, wherein the liquid material is formed from recycled condensation mixture to which an external auxiliary liquid is added, introduction of which in an amount of at least 5% by weight, based on the condensation mixture, reduces the freezing point of the condensation mixture to below −12° C.

8. A process as claimed in claim 1, wherein the temperature of the liquid condensation mixture is lower than the saturation vapor temperature of the vapor phase.

9. A process as claimed in claim 1, wherein the recycle ratio for introducing the condensation mixture into the condensation zone is from 10:1 to 150:1, based on kg/h of recycled condensation mixture to kg/h of nonrecycled condensation mixture.

10. A process as claimed in claim 1, wherein the vapor phase is mixed with the liquid material by at least one step selected from the group consisting of spraying the liquid material, and trickling the liquid material over at least one member selected from the group consisting of apparatus surfaces, baffles, and packings of the condenser.

11. A process for purifying acrylic acid by crystallization by means of vacuum evaporation, wherein a solution which contains acrylic acid and water and may contain further components is crystallized by means of vacuum evaporation with formation of a liquid phase, consisting of a mother liquor containing from 10 to 34% by weight of water and of the crystals, and a vapor phase, the vapor phase is introduced into a liquid material in a condensation zone with formation of a liquid condensation mixture, and the liquid condensation mixture is recycled at least partly to the condensation zone, the operating conditions in the condensation zone being established so that no solid is precipitated therein.

12. A process as claimed in claim 11, wherein the liquid material used is a one-phase liquid mixture having an acrylic acid content of from 50 to 70% by weight, based on 100% by weight of acrylic acid and water.

13. A process as claimed in claim 11, wherein the liquid material is formed from recycled condensation mixture to which an internal auxiliary liquid having an acrylic acid content of at least 65% by weight, based on 100% by weight of acrylic acid and water, is added, this auxiliary liquid being selected from the group consisting of solution to be crystallized, mother liquor arriving from the crystallization, liquid phase which contains crystals, and a mixture thereof.

14. A process as claimed in claim 11, wherein the liquid material is formed from recycled condensation mixture to which an external auxiliary liquid is added, introduction of which in an amount of at least 5% by weight, based on the condensation mixture, reduces the freezing point of the condensation mixture to below −12° C.

15. A process as claimed in claim 11, wherein the temperature of the liquid condensation mixture is lower than the saturation vapor temperature of the vapor phase.

16. A process as claimed in claim 11, wherein the recycle ratio for introducing the condensation mixture into the condensation zone is from 10:1 to 150:1, based on kg/h of recycled condensation mixture to kg/h of nonrecycled condensation mixture.

17. A process as claimed in claim 11, wherein the vapor phase is mixed with the liquid material by at least one step selected from the group consisting of spraying the liquid material, and trickling the liquid material over at least one member selected from the group consisting of apparatus surfaces, baffles, and packings of the condenser.

18. A process for purifying acrylic acid by crystallization by means of vacuum evaporation, wherein a solution which contains acrylic acid and water and may contain further components is crystallized by means of vacuum evaporation with formation of a liquid phase, consisting of a mother liquor containing from 10 to 34% by weight of water and of the crystals, and a vapor phase, the vapor phase is introduced into a liquid material in a condensation zone with formation of a liquid condensation mixture, and the liquid condensation mixture is recycled at least partly to the condensation zone, the operating conditions in the condensation zone being established so that no solid is precipitated therein, wherein the liquid material is formed from recycled condensation mixture to which an internal auxiliary liquid having an acrylic acid content of at least 65% by weight, based on 100% by weight of acrylic acid and water, is added, this auxiliary liquid being selected from the group consisting of solution to be crystallized, mother liquor arriving from the crystallization, liquid phase which contains crystals, and a mixture thereof, and wherein the temperature of the liquid condensation mixture is lower than the saturation vapor temperature of the vapor phase.

* * * * *